US010154697B2

(12) United States Patent
Kasahara

(10) Patent No.: US 10,154,697 B2
(45) Date of Patent: Dec. 18, 2018

(54) NECK SUPPORTER

(71) Applicants: Yukari Corporation, Kanagawa (JP);
Sole Balance Laboratory Co., Ltd.,
Kanagawa (JP)

(72) Inventor: Iwao Kasahara, Kanagawa (JP)

(73) Assignees: Yukari Corporation (JP); Sole
Balance Laboratory Co., Ltd (JP)

(*) Notice: Subject to any disclaimer, the term of this patent is extended or adjusted under 35 U.S.C. 154(b) by 257 days.

(21) Appl. No.: 14/339,940

(22) Filed: Jul. 24, 2014

(65) Prior Publication Data
US 2014/0331397 A1 Nov. 13, 2014

Related U.S. Application Data

(63) Continuation of application No. PCT/JP2012/051614, filed on Jan. 26, 2012.

(51) Int. Cl.
A41D 13/05 (2006.01)
A61F 5/055 (2006.01)
(Continued)

(52) U.S. Cl.
CPC ..... A41D 13/0512 (2013.01); A41D 13/0155 (2013.01); A61F 5/055 (2013.01); A61F 5/05816 (2013.01)

(58) Field of Classification Search
CPC . A41D 13/0155; A41D 13/0512; A61F 5/055; A61F 5/05816
See application file for complete search history.

(56) References Cited

U.S. PATENT DOCUMENTS 2,911,970 A * 11/1959 Bartels ............... A61F 5/055
128/DIG. 23
3,164,151 A * 1/1965 Vere Nicoll ......... A61F 5/012
128/DIG. 23
(Continued)

FOREIGN PATENT DOCUMENTS

CN 1170562 A 1/1998
CN 2748048 Y 12/2005
(Continued)

OTHER PUBLICATIONS

International Search Report for corresponding application No. PCT/JP2012/051614, dated Feb. 8, 2012.
(Continued)

Primary Examiner — Anna Kinsaul
(74) Attorney, Agent, or Firm — Duquette Law Group, LLC

(57) ABSTRACT

Provided is a neck supporter which is easy to use and which can reliably support the head of the wearer. The neck supporter includes an elongated main body providing said air-bag; an air injection valve that is provided in said main body to enable the air to be injected into said air-bag or discharged therefrom; connection sections (e.g., loops and hooks) that are provided on opposite surfaces in a vicinity of opposite ends of said main body to connect said opposite surfaces to each other; and a plurality of retaining portions (e.g., thermal compression bonding portions and through-holes) that are provided dispersedly as dots in series in a longitudinal direction of said main body to provide bonded portions between a front surface and a back surface of said main body.

5 Claims, 6 Drawing Sheets

(51) Int. Cl.
A61F 5/058 (2006.01)
A41D 13/015 (2006.01)

(56) References Cited

U.S. PATENT DOCUMENTS

D263,625 S * 3/1982 McKnight .................... D24/191
5,060,661 A * 10/1991 Howard .................. A61F 5/055
  128/845
6,165,146 A * 12/2000 Giebeler ................. A61F 5/055
  602/18

FOREIGN PATENT DOCUMENTS

| | | |
|---|---|---|
| GB | 2477778 A | 8/2011 |
| JP | 4926190 Y1 | 7/1974 |
| JP | 1997098996 | 4/1997 |
| JP | 3074457 U | 1/2001 |
| JP | 3084442 | 12/2001 |
| JP | 2006197953 A | 8/2006 |
| JP | 2008011969 A | 1/2008 |
| KR | 20030065785 A | 8/2003 |
| WO | 2008035680 A1 | 3/2008 |

OTHER PUBLICATIONS

Extended European Search Report dated Sep. 14, 2015 from corresponding European Application No. EP12866597.

* cited by examiner

Fig. 3(a)
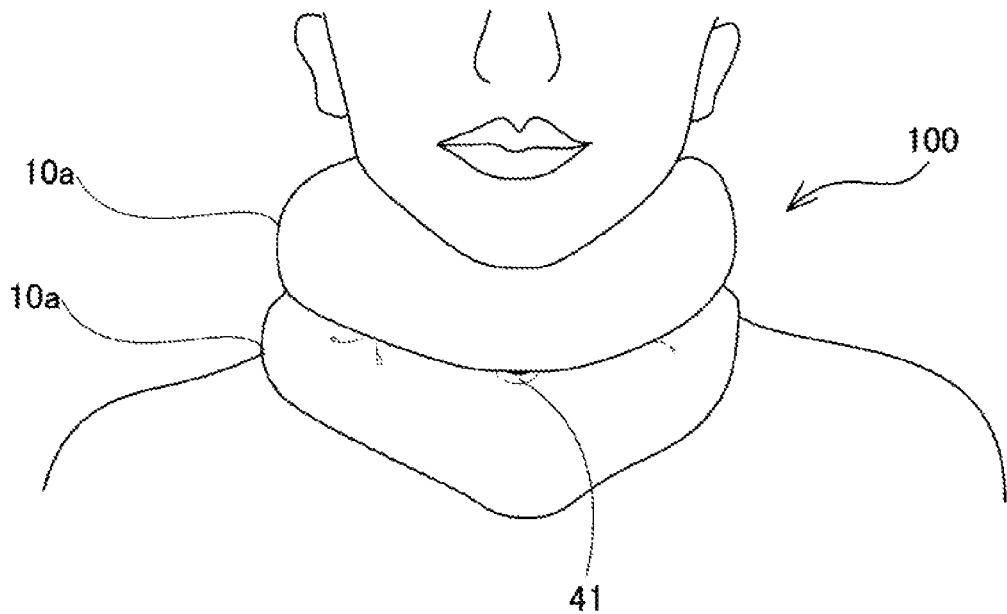
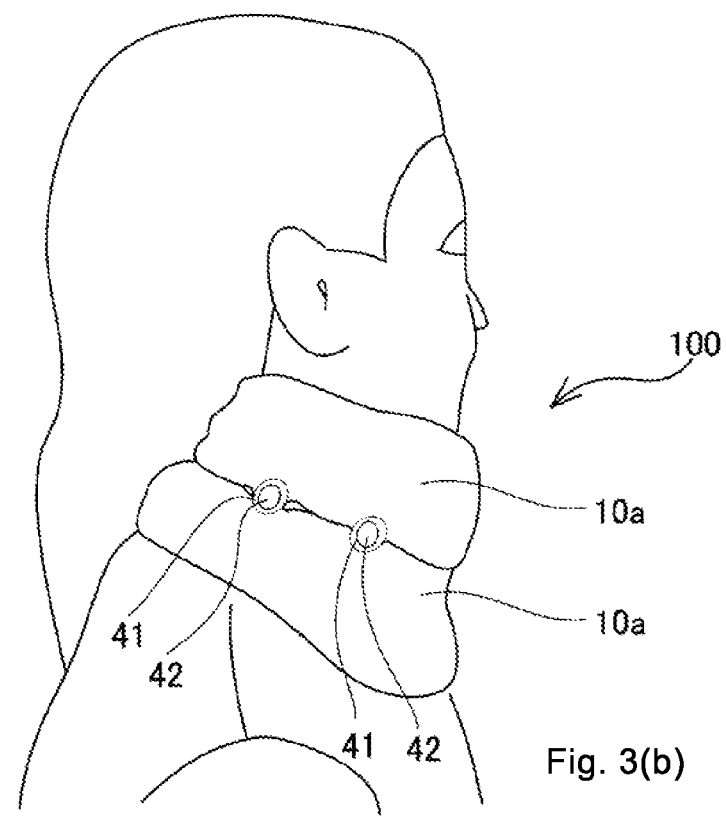
Fig. 3(b)

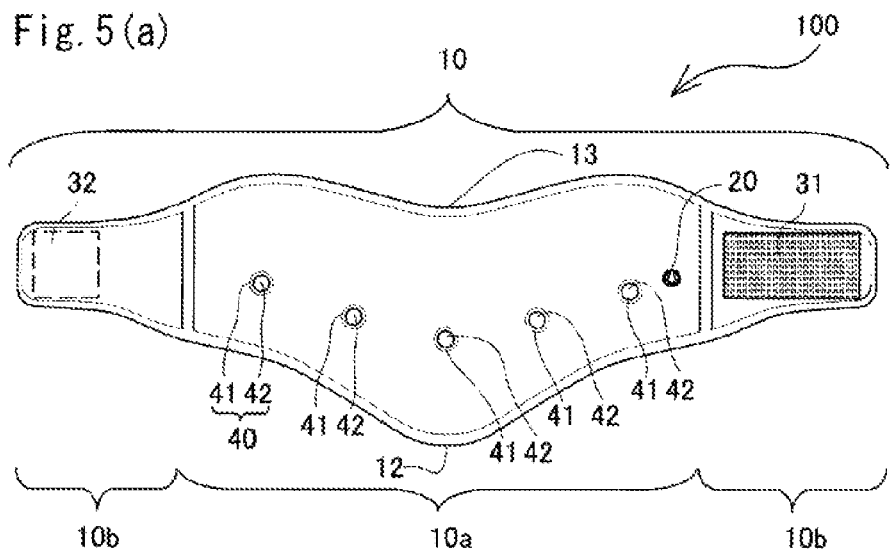
Fig. 5(a)
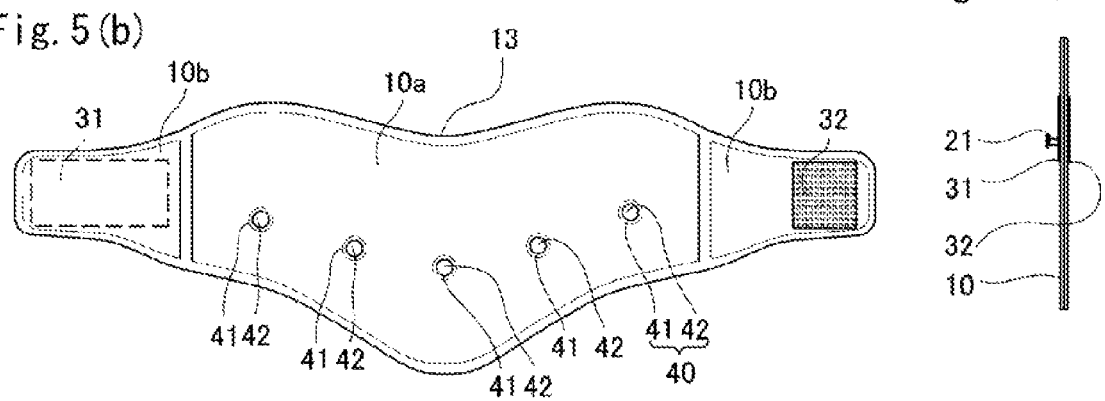
Fig. 5(b)
Fig. 5(c)
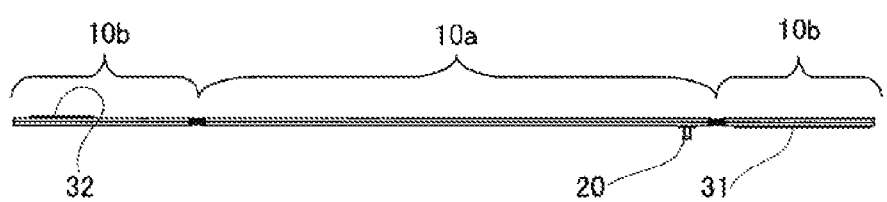
Fig. 5(d)
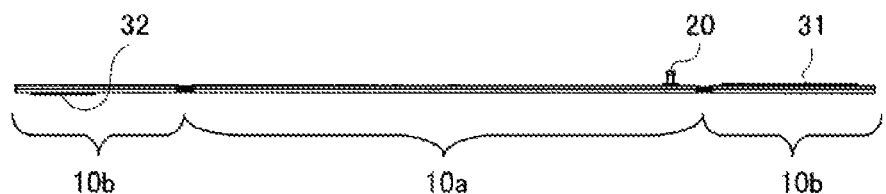
Fig. 5(e)

US 10,154,697 B2

NECK SUPPORTER

RELATED APPLICATIONS

This application is a continuation of International Application No. PCT/JP2012/051614, filed Jan. 26, 2012, now pending, the contents of which is incorporated herein by reference.

FIELD

The present invention relates to a neck supporter, which is to be fit around a neck of a wearer to support a head of the wearer and has an air-bag in which air is to be injected, and in particular to a neck supporter, which is to be used most appropriately during a desk work using a personal computer or the like, or during a travelling time over a long distance by an airplane or a bullet train.

BACKGROUND

A conventional simplified corset for neck is prepared by providing parallelly, between a chin-receiving tube, which has been formed in the form of a ring that permits to surround a neck of a patient, to encompass the upper region of the neck, which extends from the chin to the rear side of the neck, so as to support the upper region of the neck of the patient, and a lower side supporting tube to encompass the lower region of the neck in the similar manner, a plurality of bellows-shaped pillar tubes for supporting the chin-receiving tube in the vertical direction of the neck to form openings, thus preparing a corset. These tubes are made of soft synthetic resin, so that they can inflate or deflate by supplying air to them or discharging it from them, and they can expand like a balloon by supplying the air through supplying/discharging air ports (air injection ports) (see for example Japanese Utility Model Registration No. 3084442).

SUMMARY

However, the conventional simplified corset for neck has problems that the chin-receiving tube, the lower side supporting tube and four supporting tubes are independent, thus making it necessary to inject the air through the air injection ports respectively provided in the tubes, and the usage of it is not easy.

In addition, the conventional simplified corset for neck has a further problem that a ratio of the openings to the region placed between the chin-receiving tube and the lower side supporting tube is high, thus disabling the head of the wearer from being fully supported by the supporting tubes.

An object of the present invention, which was made to solve the problems as described above, is to provide a neck supporter in which the usage is easy and the head of the wearer can securely be supported.

Embodiments of the present innovation relate to a neck supporter according to the present invention, which is to be fit around a neck of a wearer and has an air-bag in which air is to be injected, the neck supporter comprises: an elongated main body providing the air-bag; an air injection valve that is provided in the main body to enable the air to be injected into the air-bag or discharged therefrom; connection sections that are provided on opposite surfaces in a vicinity of opposite ends of the main body to connect the opposite surfaces to each other; and a plurality of retaining portions that are provided dispersedly as dots in series in a longitudinal direction of the main body to provide bonded portions between a front surface and a back surface of the main body.

Effects of the Invention

In to the neck supporter according to the present invention, it is possible to discharge air from the air bag, when not in use, to fold into a portable small size. In the neck supporter according to the present invention, air is injected into the air bag, when in use, to fill the main body with the air, so as to create a double inflated unit with a boundary as a straight line connecting a plurality of through-holes. Thus, in the neck supporter according to the present invention, the lower side of the main body comes into contact with the shoulders of the wearer, and the lower inflated section supports the upper inflated section, and the upper side of the main body comes into contact with the lower side of the chin of the wearer, with the result that the head of the wearer can securely be supported on the shoulders of the wearer through the main body.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

FIG. 3(a) is a front view illustrating a wearing state of the neck supporter as shown in FIG. 1, and FIG. 3(b) is a side view illustrating a wearing state of the neck supporter as shown in FIG. 1;

FIG. 5(a) is a front view illustrating a schematic structure of a neck supporter according to the second embodiment of the present invention, FIG. 5(b) is a rear view of the neck supporter as shown in FIG. 5(a), FIG. 5(c) is a right-side view of the neck supporter as shown in FIG. 5(a), FIG. 5(d) is a plan view of the neck supporter as shown in FIG. 5(a), and FIG. 5(e) is a bottom view of the neck supporter as shown in FIG. 5(a)

DETAILED DESCRIPTION

First Embodiment

Figure 1A:
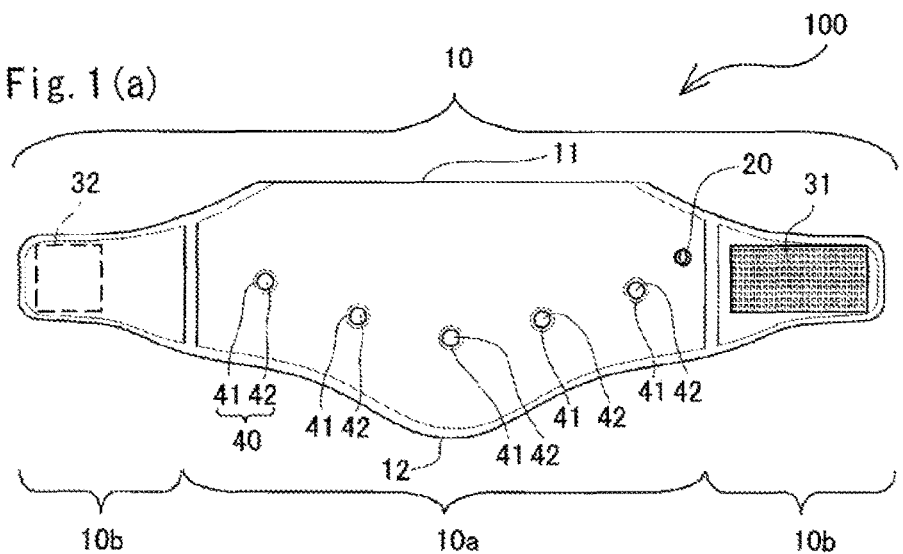
FIG. 1(a) is a front view illustrating a schematic structure of a neck supporter according to the first embodiment of the present invention.

A neck supporter 100 comprises, as shown in FIG. 1, comprises: an elongated main body 10 providing an air-bag, in which air is to be injected; an air injection valve 20 that is provided in the main body 10 to enable the air to be injected into the air-bag or discharged therefrom; connection sections 31, 32 that are provided on opposite surfaces in a vicinity of opposite ends of the main body 10 to connect the opposite surfaces to each other; and a plurality of retaining portions 40 that are provided dispersedly as dots in series in a longitudinal direction of the main body 10 to provide bonded portions between a front surface and a back surface of the main body 10. The front surface of the main body 10, which corresponds to FIG. 1(a), is a surface on which the air injection valve 20 is provided, and the back surface of the main body 10, which corresponds to FIG. 1(b), is a surface, which is to be brought into contact with a neck of a wearer.

The main body 10 according to this embodiment of the present invention is provided with a linear portion 11 having substantially the linear shape in the vicinity of the central area on the upper side, and a bulge portion 12 having the central area on the lower side curving downward so that the almost central point is placed at the lowermost position. It is made of a sheet of synthetic resin (for example, polyvinyl chloride: PVC) which is line-symmetric with respect to the linear portion 11 as a line-symmetric axis, and formed into a bag body by folding the synthetic resin sheet at the linear portion 11 and bonding, by a thermal compression bonding, its inner surface on its periphery excluding the above-mentioned linear portion 11.

Figure 2A:
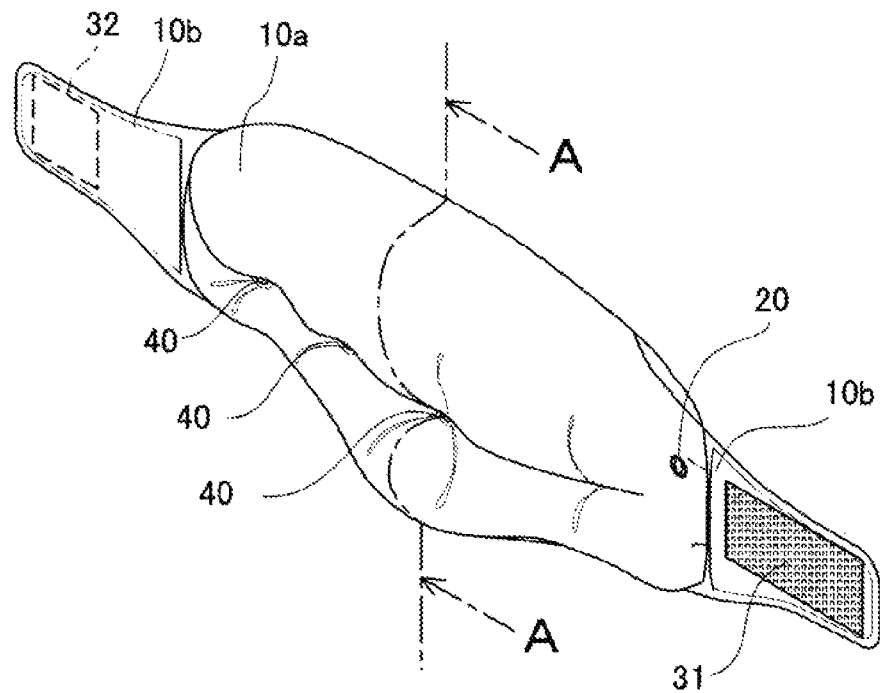
FIG. 2(a) is a perspective view illustrating a state in which air is injected into the neck supporter as shown in FIG. 1.

More specifically, in the main body 10, the inner surface of the synthetic resin sheet is bonded by the thermal compression bonding so that bonded regions cross between the upper side and the lower side of the main body in the vicinity of its both ends, to provide sectioned regions, i.e., a region into which air is to be injected (hereinafter referred to as the "injection region 10a") and regions into which air is not to be injected (hereinafter referred to as the "non-injection region 10b). The connection sections 31, 32 are provided in the non-injection region 10b. The non-injection region 10b can be kept flat by providing the connection sections 31, 32 in the non-injection region 10b, even when air is injected into the main body 10 (the injection region 10a) as shown in FIG. 2(a). It is therefore possible to prevent the connection sections 31, 32 from being deformed, thus ensuring the connection of the opposite ends of the main body 10 by the connection sections 31, 32.

In addition, the main body 10 according to this embodiment of the present invention has a sueded surface so that its surface has an increased friction resistance to the synthetic resin sheet. As a result, it is possible to prevent the neck supporter 100 as worn from moving to cause the neck supporter 100 to be worn at a proper position, and make the texture of the neck supporter 100 as worn good.

In this embodiment of the present invention, the neck supporter 100 using a hook and loop fastener as the connection sections 31, 32 will be described. The present invention is not limited only to such a hook and loop fastener, but there may be used any device by which the opposite ends of the main body 10 can be connected to each other, for example, a button, a dot-button, a snap, a hook, a buckle, a fastener (a zipper, a zip fastener), a skirt-hook, or a spindle stopper.

Figure 1B:
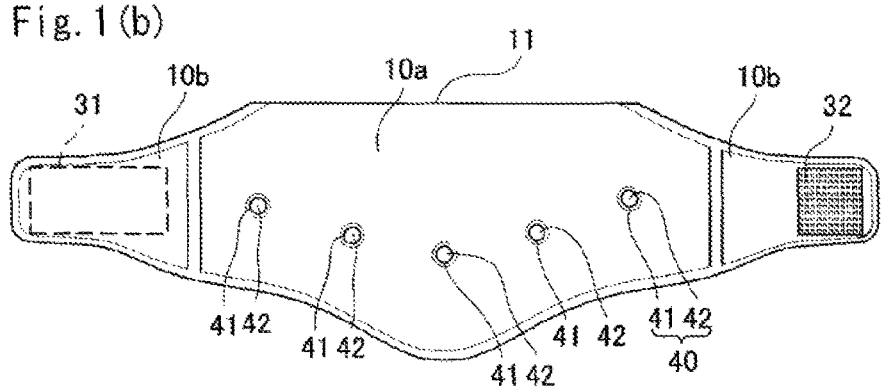
FIG. 1(b) is a rear view of the neck supporter as shown in FIG. 1(a)
Figure 1C:
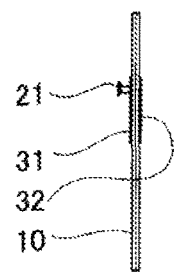
FIG. 1(c) is a right-side view of the neck supporter as shown in FIG. 1(a)
Figure 1D:
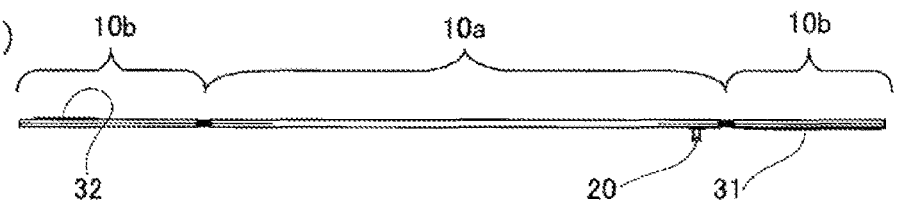
FIG. 1(d) is a plan view of the neck supporter as shown in FIG. 1(a)
Figure 1E:
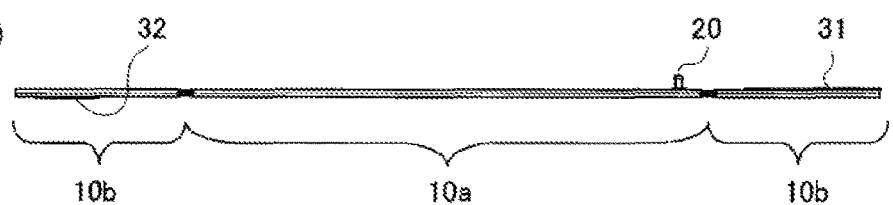
FIG. 1(e) is a bottom view of the neck supporter as shown in FIG. 1(a)

The main body 10 according to this embodiment of the present invention has loops 31 of the hook and loop fastener provided on the front surface at the right-hand side as shown in FIG. 1(a), and hooks 32 of the hook and loop fastener provided on the back surface at the right-hand side as shown in FIG. 1(b). However, the hooks 32 may be provided on the front surface and the loops 31 may be provided on the back surface. The position at which the loops 31 are to be provided on the front surface may be changed from the right-hand side to the left-hand side and the position at which the hooks 32 are to be provided on the back surface may be changed from the right-hand side to the left-hand side.

The retaining portions 40 according to this embodiment of the present invention are provided, a plurality of positions in the injection region 10a (for example at five positions), with thermal compression bonding portions 41 having substantially the circular shape, which are formed in an L-shape form along the lower side of the main body 10, by bonding the synthetic resin sheet on the inner surface to each other by the thermal compression bonding, and with through-holes 42 having substantially the circular shape, which are formed by removing substantially the central areas of the thermal compression bonding portions 41 so as to pass through the front surface and the back surface of the main body 10 and to be formed concentrically with respect to the thermal compression bonding portions 41. The retaining portions 40 are provided so that the distance between the upper side of the main body 10 and the respective retaining portion 40 is larger than the distance between the lower side of the main body 10 and the respective corresponding retaining portion 40.

The retaining portion 40 may not always be provided with the through-hole 42. However, the through-hole 42 serves as a ventilation hole communicating the neck of the wearer with the outside of the neck supporter 100, thus making it possible to improve air permeability of the neck supporter 100 and inhibit the neck from becoming damp around the neck of the wearer when wearing the neck supporter 100 for a long period of time.

Now, description will be given below about how to use the neck supporter 100 according to this embodiment of the present invention, with reference to FIGS. 1 to 3.

Figure 2B:
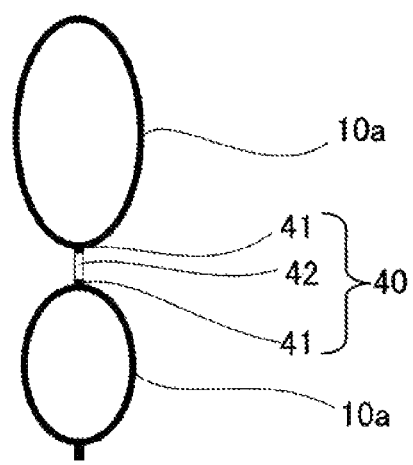
FIG. 2(b) is a cross-sectional view of the neck supporter, cut along the line A-A as shown in FIG. 2(a)
Figure 4A:
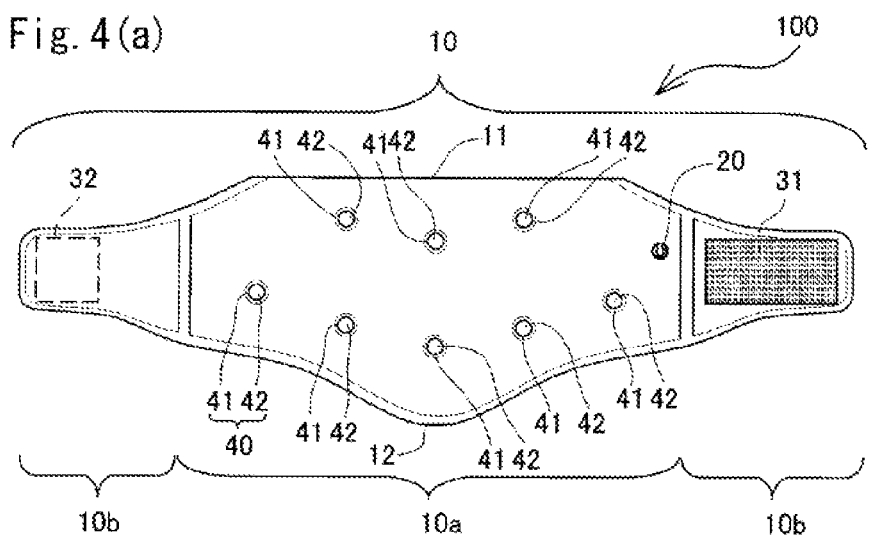
FIG. 4(a) is a front view illustrating a schematic structure of the other neck supporter according to the first embodiment of the present invention.
Figure 4B:
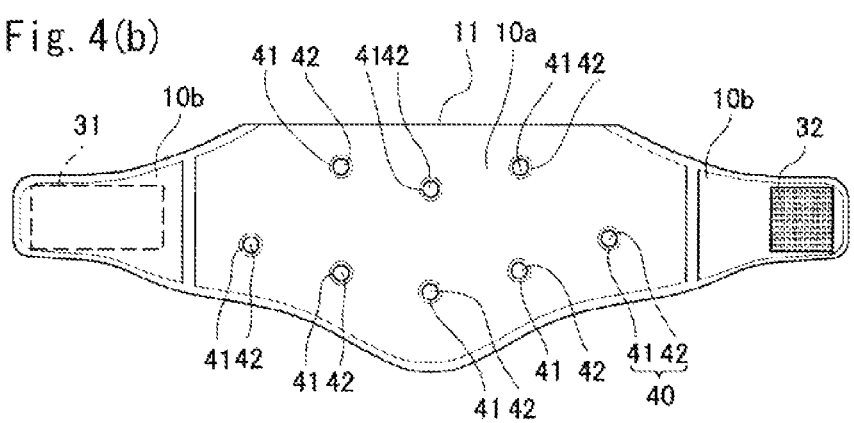
FIG. 4(b) is a rear view of the neck supporter as shown in FIG. 4(a)
Figure 4C:
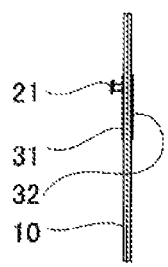
FIG. 4(c) is a right-side view of the neck supporter as shown in FIG. 4(a)
Figure 4D:
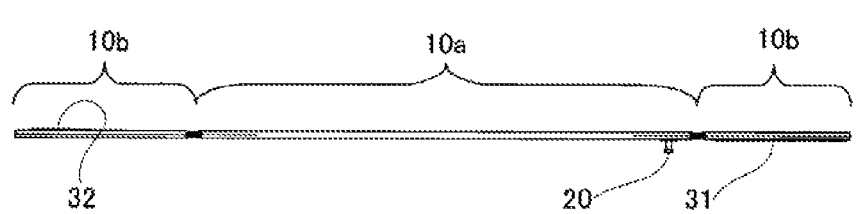
FIG. 4(d) is a plan view of the neck supporter as shown in FIG. 4(a)
Figure 4E:
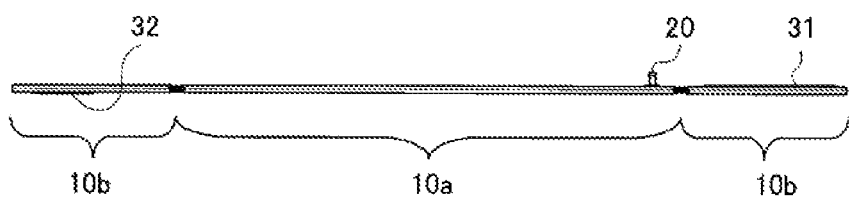
FIG. 4(e) is a bottom view of the neck supporter as shown in FIG. 4(a)

First, when a user of the neck supporter 100 injects air into the main body 10 (the injection region 10a) through the air injection valve 20 provided on the front surface of the main body 10 (see FIG. 1(a)), only the injection region 10a of the main body 10 inflates as shown in FIG. 2.

Then, the user of the neck supporter 100 closes a supplying/discharging air port of the air injection valve 20 by a plug (an external plug), with the injection region 10a of the main body 10 properly inflated. When the air is injected into the main body 10 (the injection region 10a) of the neck supporter 100 in this manner, there is created a double inflated unit with a boundary as a straight line connecting five retaining portions 40 (the thermal compression bonding portions 41, the through-holes 42).

Then, the user of the neck supporter 100 places the back surface of the main body 10 on the neck, with the bulge portion 12 of the main body 100 facing down (see FIG. 1(b)), makes a position adjustment so that the bulge portion 12 is placed just below the chin, applies the main body 10 from the front side of the neck and wraps it around the neck as shown in FIG. 3, and connects the loops 31 with the hooks 32 of the hook and loop fastener on the back side of the neck. This makes it possible to bring the lower side of the main body of the neck supporter 100 into contact with on the shoulders of the wearer so that the lower inflated section supports the upper inflated section, and to bring the upper side of the main body into contact with the lower side of the chin of the wearer, with the result that the head of the wearer can securely be supported on the shoulders of the wearer through the main body 10.

Here, it is considered that a neck failure is caused by, in addition to a weight of the head, an indirect external force derived from excessive shock wave and distortional wave transferred from an unstable sole of the foot, as repeatedly applied to the neck. In this respect, the neck supporter 100 has technical effects of supporting the head of the wearer to reduce strain on the neck, preventing deformation or strain of the first cervical vertebra of the wearer, and enhancing stability of autonomic nerves placed in clumps around a connection between the upper side of the cervical spine and a skull bone of the wearer.

The neck supporter 100 may be folded in a small size, when not in use, by discharging the air from the inside (the injection region 10a) of the main body 10. It is therefore possible to put the neck supporter 100 as folded in a bag for example during walking, and to inflate, when sitting on a seat of an airplane, a bullet train, or the like, the main body 10 to wear the neck supporter 100, thus being most suitable for a case where a plurality of transformation measures are used. The neck supporter 100 is also most suitable for use during a desk work using a personal computer, etc.

The neck supporter 100 according to this embodiment of the present invention has been described as having the five thermal compression bonding portions 41 (the through-holes 42) as the retaining portions 40 as shown in FIG. 1. However, the present invention is not limited only to the five thermal compression bonding portions 41 (the through-holes 42), provided that there is created the double inflated unit with a boundary as a straight line connecting a plurality of retaining portions 40 (the thermal compression bonding portions 41, the through-holes 42).

The neck supporter 100 according to this embodiment of the present invention has been described as the five thermal compression bonding portions 41 (the through-holes 42) as the retaining portions 40 being arranged in a row, as shown in FIG. 1. However, a plurality of (for example, five and three) thermal compression bonding portions 41 (the through-holes 42) may be arranged in two rows, as shown in FIG. 4. In this case, when the air is injected into the main body 10 (the injection region 10a) of the neck supporter 100 in this manner, there is created a triple inflated unit with boundaries as the respective straight line connecting the retaining portions 40 (the thermal compression bonding portions 41, the through-holes 42) in the respective low. The upper inflated section comes into contact with chin of the wearer, the middle inflated section comes into contact with the neck of the wearer, and the lower inflated section comes into contact with the chest of the wearer. It is therefore possible to bring the neck supporter 100 into close contact with a curved surface of the wearer from the lower side of the chin to the chest, thus enhancing the performance of supporting the neck of the wearer by the neck supporter 100.

With respect to an additional function of the neck supporter 100 according to this embodiment of the present invention, a bag may be provided along an area, in the main body, from around a connection between the upper side of the cervical spine and the skull bone of the wearer to the cervical spine, and refrigerant may be received in the bag. Such a structure permits to cool a periphery of the connection between the upper side of the cervical spine and the skull bone of the wearer, thus enhancing stability of autonomic nerves placed in clumps around the connection between the upper side of the cervical spine and the skull bone of the wearer and relieving damage of the neck or disorder due to a stiff neck.

In addition, the neck supporter 100 according to this embodiment of the present invention may be provided in the non-injection region 10b with a cushioning material. Such a structure makes it possible to relieve, when the neck supporter 100 supports slightly upward the chin of the wearer, load applied downward to the back of the neck of the wearer, thus reducing strain on the back of the neck of the wearer.

Figure 6A:
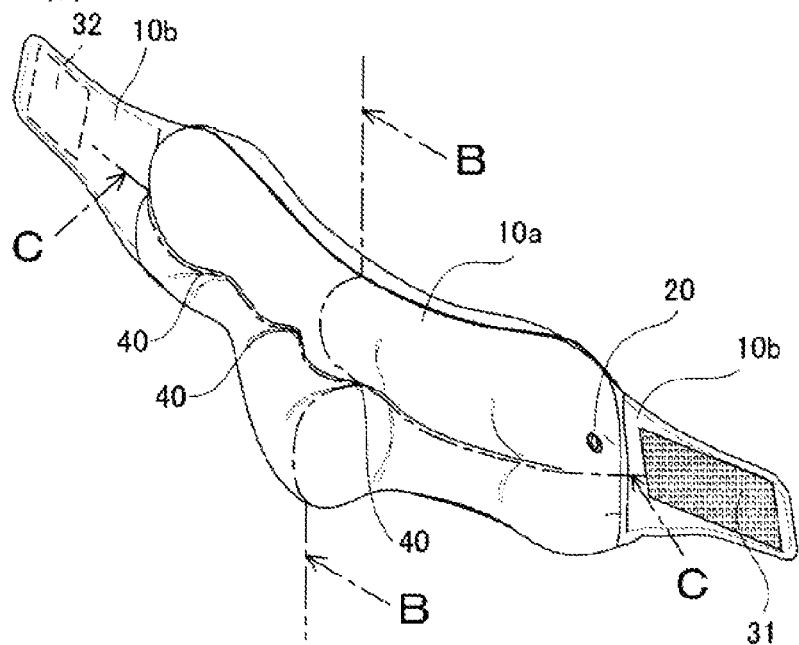
FIG. 6(a) is a perspective view illustrating a state in which air is injected into the neck supporter as shown in FIG. 5.
Figure 6B:
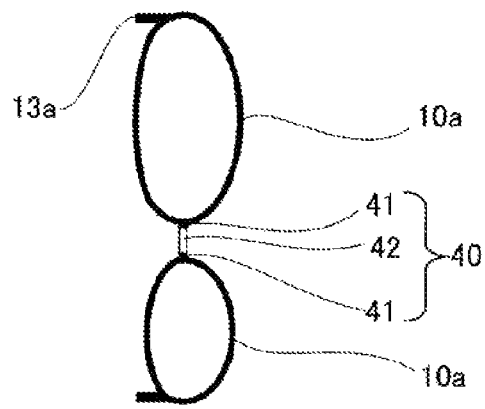
FIG. 6(b) is a cross-sectional view of the neck supporter, cut along the line B-B as shown in FIG. 6(a)
Figure 6C:
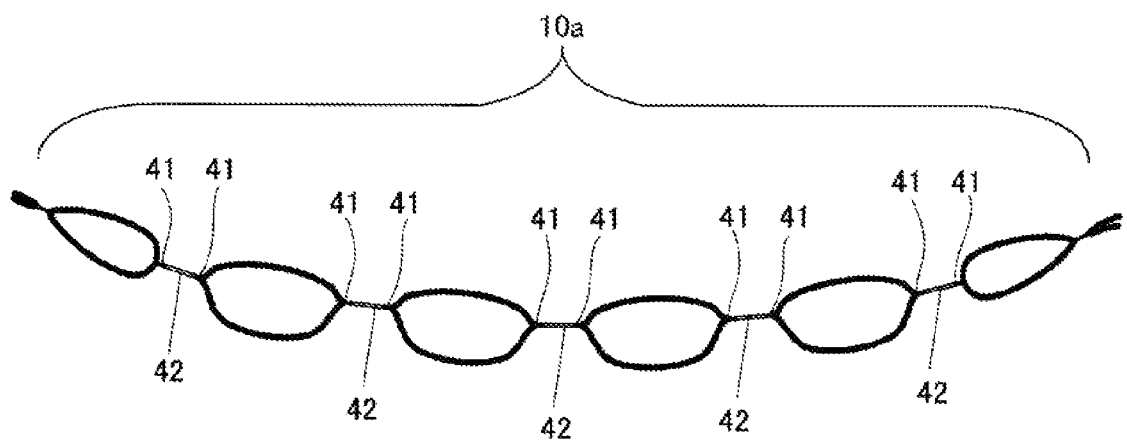
FIG. 6(c) is a cross-sectional view of the neck supporter, cut along the line C-C as shown in FIG. 6(a).

FIG. 5(a) is a front view illustrating a schematic structure of the neck supporter according to the second embodiment of the present invention, FIG. 5(b) is a rear view of the neck supporter as shown in FIG. 5(a), FIG. 5(c) is a right-side view of the neck supporter as shown in FIG. 5(a), FIG. 5(d) is a plan view of the neck supporter as shown in FIG. 5(a), and FIG. 5(e) is a bottom view of the neck supporter as shown in FIG. 5(a). FIG. 6(a) is a perspective view illustrating a state in which air is injected into the neck supporter as shown in FIG. 5, FIG. 6(b) is a cross-sectional view of the neck supporter, cut along the line B-B as shown in FIG. 6(a), and FIG. 6(c) is a cross-sectional view of the neck supporter, cut along the line C-C as shown in FIG. 6(a). In FIGS. 5 and 6, the same reference numerals as those in FIG. 1 to FIG. 4 denote the same or corresponding components, and the description of them will be omitted.

The main body 10 according to this embodiment of the present invention has substantially the V-shape, which is provided with a concave portion 13 having the central area on the upper side curving downward so that the almost central point is placed at the lowermost position, on the one hand, and with a bulge portion 12 having the central area on the lower side curving downward so that the almost central point is placed at the lowermost position. It is made of a pair of sheets of synthetic resin which form the front surface and the back surface, respectively and are formed into a bag body by bonding, by a thermal compression bonding, their inner surfaces on its periphery.

The neck supporter 100 according to this embodiment of the present invention has a technical effect of enhancing close-fitting property and stability of the neck supporter 100 relative to the neck of the wearer, by providing the concave portion 13 on the upper side of the main body to apply the upper side of the main body 10 along the line of the chin of the wearer.

With respect to the main body 10 according to this embodiment of the present invention, the front surface and the back surface are bonded, unlike the first embodiment of the present invention, also in the vicinity of the central area of the upper side by the thermal compression bonding. The thermal compression bonded portion may be harder and such a thermal compression bonded portion may project upward due to the bonding of the pair of sheets of synthetic resin having the same shape. Such a projecting portion may come into contact with the lower side of the chin of the wearer at a sharp angle, thus bringing a feeling of discomfort to the wearer.

For these reasons, the neck supporter 100 according to this embodiment of the present invention prevents the projected edge 13a from coming into contact with the lower side of the chin of the wearer at a sharp angle, by shortening the length of the front surface in the lateral direction of the main body 10 than the length of the back surface in the lateral direction of the main body 10 so that the projected edge 13a is directed outward from the wearer, as shown in FIG. 6(b).

Alternatively, in the neck supporter 100 according to this embodiment of the present invention, it is possible to curve the main body 10 in an arcuate shape toward the side of the back surface, by lengthen the length of the front surface in the longitudinal direction of the main body 10 than the length of the back surface in the longitudinal direction of the main body 10. This may provide technical effects of recognizing clearly the difference between the front surface side and the back surfaced side of the neck supporter 100 to facilitate the wearing of the neck supporter 100, and enhancing close-fitting property of the neck supporter 100 relative to the neck of the wearer.

The second embodiment of the present invention differs from the first embodiment of the present invention only in that the main body 10 is provided with the concave portion 13 on the upper side and the main body 10 is formed of the pair of sheets of synthetic resin. The second embodiment of the present invention provides the same technical effects as the first embodiment of the present invention, excepting the technical effects by the concave portion 13 and the pair of sheets of synthetic resin.

DESCRIPTION OF REFERENCE NUMERALS 10 main body
10a injection region
10b non-injection region
11 linear portion
12 bulge portion
13 concave portion
13a projected edge
20 air injection valve
31 loop
32 hook
40 retaining portion
41 thermal compression bonding portion
42 through-hole
100 neck supporter.

What is claimed is:

1. A neck supporter configured to fit around a neck of a wearer and having an air-bag configured to receive air, said neck supporter comprising:
    an elongated main body providing said air-bag, said elongated main body being provided with a bulge portion having a central area on a lower side curving downward so that a substantially central point is placed at a lowermost position;
    an air injection valve that is provided in said main body to enable the air to be injected into said air-bag or discharged therefrom;
    connection sections that are provided on opposite surfaces in a vicinity of opposite ends of said main body to connect said opposite surfaces to each other;
    a plurality of retaining portions that are provided dispersedly as dots in series in a longitudinal direction of said main body to provide bonded portions between a front surface and a back surface of said main body, the plurality of retaining portions defining a boundary as a straight line connecting said retaining portions, the boundary extending along the longitudinal direction of the elongated main body, the boundary defining the elongated main body as a double inflated unit having:
        an upper air-bag section defining a continuous chamber between both the front surface and the back surface of the main body and extending along the longitudinal direction of the elongated main body, the upper air-bag section disposed between the plurality of retaining portions and an upper side of the elongated main body, and
        a lower air-bag section defining a continuous chamber between both the front surface and the back surface of the main body and extending along the longitudinal direction of the elongated main body, the lower air-bag section disposed between the plurality of retaining portions and the lower side of the elongated main body,
    the double inflated unit configured to inflate in response to injection of air into said main body, so as to bring the bulge portion of said main body into contact with a chest of the wearer;
    a length of the front surface in the longitudinal direction of said main body is longer than a length of the back surface in the longitudinal direction of said main body; and
    a length of the front surface in a lateral direction of said main body is shorter than a length of the back surface in a lateral direction of said main body.

2. The neck supporter, as claimed in claim 1, wherein: said main body has a bulge portion, which curves downward in a vicinity of a central area of an upper side.

3. The neck supporter of claim 1, wherein the boundary defines the elongated main body as a single double inflated unit having:
    a single upper air-bag section extending along the longitudinal direction of the elongated main body and disposed between the plurality of retaining portions and an upper side of the elongated main body; and
    a single lower air-bag section extending along the longitudinal direction of the elongated main body and disposed between the plurality of retaining portions and the lower side of the elongated main body.

4. The neck supporter of claim 1, wherein a distance between the upper side of the elongated main body and the plurality of retaining portions is larger than the distance between the lower side of the elongated main body and the plurality of retaining portions.

5. The neck supporter of claim 1, wherein the plurality of retaining portions are disposed in an L-shape in proximity to the lower side of the elongated main body.

* * * * *